United States Patent
Tu et al.

[11] Patent Number: 5,938,659
[45] Date of Patent: Aug. 17, 1999

[54] CATHETER SYSTEM HAVING COOLED MULTIPLE-NEEDLE ELECTRODE AND METHODS THEREOF

[75] Inventors: Hosheng Tu, Tustin; Weng-Kwen Raymond Chia, Irvine, both of Calif.

[73] Assignee: Irvine Biomedical, Inc., Irvine, Calif.

[21] Appl. No.: 09/065,230

[22] Filed: Apr. 20, 1998

Related U.S. Application Data

[62] Division of application No. 08/856,726, May 15, 1997, Pat. No. 5,792,140.

[51] Int. Cl.$^6$ .................................................. A61B 17/39
[52] U.S. Cl. ............................... 606/41; 607/101; 607/122
[58] Field of Search ........................... 606/41, 42, 48–50; 607/98–105, 113, 122

[56] References Cited

U.S. PATENT DOCUMENTS

| 5,487,385 | 1/1996 | Avitall | 607/122 |
| 5,643,197 | 7/1997 | Brucker et al. | 607/122 |
| 5,688,267 | 11/1997 | Panescu et al. | 606/41 |
| 5,697,927 | 12/1997 | Imran et al. | 606/41 |

*Primary Examiner*—Linda C. M. Dvorak
*Assistant Examiner*—Roy Gibson

[57] ABSTRACT

A method for operating a steerable ablation catheter having at least one multiple-needle electrode at the tip section of an inner catheter within a heart chamber, wherein the ablation catheter including at least one multiple-needle electrode is inserted into a chamber of the heart to create a plurality of deep, large, and contiguous lesions by applying radiofrequency energy and cooled fluid to the electrode.

5 Claims, 5 Drawing Sheets

CATHETER SYSTEM HAVING COOLED MULTIPLE-NEEDLE ELECTRODE AND METHODS THEREOF

This is a division of Ser. No. 08/856,726, filed May 15, 1997 now U.S. Pat. No. 5,792,140.

FIELD OF THE INVENTION

The present invention generally relates to improved constructions for a cardiovascular catheter. More particularly, this invention relates to catheter and methods for ablating cardiac tissues via a steerable ablation catheter having at least one cooled multiple-needle electrode which has irrigation capabilities for ablating intracardiac tissues resulting in a plurality of deeper and larger lesions in the myocardium of the heart.

BACKGROUND OF THE INVENTION

Symptoms of abnormal heart rhythms are generally referred to as cardiac arrhythmias, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of normal pathways which are responsible for the propagation of electrical signals from upper to lower chamber necessary for performing normal systole and diastole function. The presence of arrhythmogenic site or accessory pathway can bypass or short circuit the normal pathway, potentially resulting in very rapid heart contractions, referred to here as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablating the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the tip electrode to the cardiac tissue in order to ablate the tissue of arrhythmogenic site or the accessory pathway. By successfully destroying that tissue, the abnormal signal patterns responsible for the tachycardia may be eliminated. However, in the case of atrial fibrillation (AFib), multiple arrhythmogenic sites and/or multiple accessory pathways exist. The conventional catheter with a single ablation tip electrode can not effectively cure the symptoms.

Atrial fibrillation is believed to be the result of the simultaneous occurrence of multiple wavelets of functional re-entry of electrical impulses within the atria, resulting in a condition in which the transmission of electrical activity becomes so disorganized that the atria contracts irregularly. Once considered a benign disorder, AFib now is widely recognized as the cause of significant morbidity and mortality. The most dangerous outcome from AFib is thromboembolism and stroke risk, the latter due to the chaotic contractions of the atria causing blood to pool. This in turn can lead to clot formation and the potential for an embolic stroke. According to data from the American Heart Association, about 75,000 strokes per year are AFib-related.

A catheter utilized in the endocardial radiofrequency ablation is inserted into a major vein or artery, usually in the neck or groin area. For epicardial ablation, a catheter is percutaneously introduced into the chest cavity through a small surgery hole, followed by penetrating through a punctured hole through the pericardium into the epicardial cavity. The tip section of a catheter is referred to here as the portion of that catheter shaft containing the electrode or electrodes which may be deflectable. In one embodiment, the catheter is then guided into the appropriate chamber of the heart by appropriate manipulation through the vein or artery. The tip of a catheter must be manipulatable by a physician from the proximal end of the catheter, so that the electrode at the tip section can be positioned against the tissue site to be ablated. The catheter must have a great deal of flexibility in order to follow the pathway of major blood vessels into the heart. It must permit user manipulation of the tip even when the catheter body is in a curved and/or twisted configuration. The tip section of a conventional electrophysiology catheter that is deflectable usually contains one large electrode about 4 mm in length for ablation purpose. The lesion is generally not deep because of a flat contact surface between the electrode and tissues, and because of short energy delivery period due to potential impedance increase at the ablation site.

After the exact location of a target tissue is identified, the ablation catheter may still not easily approach the target site even with assistance of an internal viewing means, such as an endoscope. This viewing situation may turn into a nightmare when an endoscope approach becomes prohibitive or unavailable during procedures. An external ultrasonic imaging capability therefore becomes in need so that ablation is not taking place in an inappropriate location. In the U.S. Pat. No. 4,794,931, there has been disclosed a catheter and system which can be utilized for ultrasonic imaging. However, there is no disclosure to how such an catheter and system can be utilized in conjunction with an endocardial or epicardial ablation catheter having multiple-needle electrodes to achieve the desired ultrasonic imaging and ultimately the desired ablation.

Imran in U.S. Pat. No. 5,281,218 teaches a needle electrode attached on a catheter for radiofrequency ablation. Though a needle-like electrode is beneficial to ablate a tissue point for deep lesion, it is not possible to make a plurality of deeper and larger lesions in a region such as in the case of atrial fibrillation or in the case of epicardial side of the myocardium. Imran does not disclose a cooled multiple-needle electrode to enhance the RF energy delivery for multiple deeper and larger lesions. For atrial fibrillation treatment, the limitation of the said technique is obvious because of its single ablation point without cooled multiple-needle electrodes.

While a radiofrequency electrophysiology ablation procedure using an existing catheter has had promising results, the tip section of a known catheter usually have only one large electrode or one needle electrode without cooling capabilities for ablation purpose. Therefore there is a need for a new and improved catheter for making a plurality of deeper and larger lesions in the myocardium or epicardium of the heart.

SUMMARY OF THE INVENTION

In general, it is an object of the present invention to provide a method employing an improved ablation catheter with at least one cooled multiple-needle electrode which can be used in ablating the arrhythmogenic region instead of an arrhythmogenic point of a patient. This method and catheters is particularly useful for treating the patient with atrial fibrillation (AFib) indications. In one embodiment, an ablation catheter comprises a delivery catheter having a distal end, a proximal end and at least one lumen extending therebetween. A handle is attached to the proximal end of the said delivery catheter.

The delivery catheter has an electrode deployment means. The electrode deployment means includes a retractable inner catheter having a tip section, comprising at least one multiple-needle electrode. The inner catheter comprises a distal end, a proximal end, and at least a central lumen extending therebetween. The proximal end of the inner catheter is attached to the electrode deployment means which comprises a push-pull mechanism on the handle. In one embodiment, the multiple-needle electrode is the tip electrode. At least one band electrode which may contain multiple needles, is spaced at a predetermined distance from the preceding electrode. In an alternate embodiment, the multiple-needle electrode contains a plurality of needles on the said electrode. In a further embodiment, at least one needle on at least one electrode faces outward toward the tissue surface to be ablated in endocardial ablation procedures or faces inward toward the epicardial tissue surface in epicardial ablation procedures. Therefore, at ablation time, the needles are positioned essentially perpendicular to the tissues to be ablated. In still another embodiment, the needles face at different directions so as to contact the endocardial tissue when a bidirectional deflectable catheter is used in the ablation procedure. The inner catheter has a nondeployed state when it is positioned in the delivery catheter. This non-deployed state is maintained during the ablation catheter insertion operation into a patient and during withdrawal of the catheter from a patient.

The ablation catheter further comprises a steering mechanism at the handle for controlling the deflection of the said multiple-needle electrode. Usually a rotating ring or a push-pull plunger is employed in the steering mechanism. In another embodiment, the steerable ablation catheter comprises a bidirectional deflection or multiple curves deflection of the tip section having at least one multiple-needle electrode. One end of the steering wire is attached at certain point of the tip section of the said inner catheter. The other end is attached to the steering mechanism at the handle. The steering mechanism on a steerable catheter or device is wellknown to those who are skilled in the art.

The inner catheter has a deployed state when it is advanced out of the distal end of the said delivery catheter. Deployment of the inner catheter is accomplished by a pushing action on the push-pull deployment mechanism at the handle. In one particular embodiment, the tip section of the deployed inner catheter has a preformed shape so that the electrode of the multiple-needle electrodes would extend outwardly of the delivery catheter when deployed. The degree of deployment is controlled by the pushing action at the said push-pull mechanism on the handle and is proportional to the push distance on the push-pull plunger of the push-pull mechanism which is quantifiable and controllable.

The deployed inner catheter having at least one multiple-needle electrode, wherein the needle has a flat top with a circular ring and an outlet port at its flat top. The flat top is provided with at least one drainage trough at its flat top for fluid to discharge from the side of the flat top. The flat top circular ring of the needles of each electrode may be positioned at the forward side facing the target tissue. After finishing the ablation operation, the retraction of the inner catheter is accomplished by pulling back axially the inner catheter relative to the delivery catheter. The degree of retraction is mainly controlled by the pulling action at the push-pull mechanism on the handle.

A fluid conveying lumen is associated with the elongate catheter shaft, and preferably is disposed within the inner catheter along the longitudinal axis thereof. The lumen is adapted to communicate with a fluid supply source to convey fluid from the source and through the lumen to be discharged through an outlet port disposed at the distal tip of the hollow needles of the electrodes.

The invention also comprises a method and system for controlling the flow rate of fluid through the lumen to optimize the cooling of the energy delivering electrode of the catheter. The control system preferably regulates the flow rate based on signals representative of the temperature of the catheter tip and/or tissue impedance.

At least one conducting wire which is soldered to the electrode passes through the lumen of the inner catheter and the interior void of the handle and is thereafter soldered to a contact pin of the connector secured at the proximal end of the handle. Therefrom, the conducting wire is connected to an external RF generator for ablation operations and/or to an EKG monitor for recording and display of the endocardial or epicardial electrical signal.

In an additional embodiment, the ablation system further comprises a temperature sensing and close-loop temperature control mechanism for the electrode having at least one temperature sensor at the tissue contact site of the electrodes. The location of the temperature sensor is preferably in the very proximity of one of the needles of the electrodes.

In a particular embodiment, the length of the multiple-needle electrode is 4 mm or longer. In an alternate embodiment, the needles on an electrode are equally spaced and the distance between the needle tip is 4 mm or less. The height of the needle is usually 1 mm or less. The material for the multiple-needle electrodes may consist of conductive metals such as platinum, iridium, gold, silver, stainless steel, Nitinol, or an alloy of their mixture.

In a still further embodiment, the tip section of the inner catheter comprising the electrodes is formed of a conducting material without catheter shaft. The multiple-needle electrode in this embodiment is formed of a flexible metal mesh or metal coil that can be retracted into the delivery catheter during inserting and withdrawal of the said catheter system in an electrophysiology procedure. In order to provide increased torsional rigidity to the catheter shaft, the shaft material preferably comprises a polymeric tube having a Durometer in the range from 30 D to 90 D, usually from 40 D to 65 D. Preferably, the shaft has a composite structure including a base layer of a relatively low Durometer material, a stiffening layer, for example, metal braid or coil, and an outer layer comprising the biocompatible polymeric material or the material that may render itself biocompatible by surface treatment. To enhance biocompatibility, the catheter shaft further comprises surface coating of heparin on the surface of the catheter shaft. It is hypothesized that the coated heparin forms a barrier, while not releasing heparin from the said surface, between the blood and the catheter surface to enhance biocompatibility during electrophysiology procedures. In a further embodiment, an ablation catheter further comprises construction of low surface energy substrates or surface treatment of low surface energy substrates, such as Teflon® type fluorinated polymers, to mitigate blood coagulation during high energy ablation. Fluorinated polymer can be the construction material for the catheter system or deposited on the shaft surface via plasma coating technology or the like.

A method for operating a steerable ablation catheter system having at least one multiple-needle electrode at the tip section of an deployable inner catheter within a heart chamber comprises percutaneously introducing the delivery catheter through a blood vessel to the heart chamber, wherein the multiple-needle electrode is deployed by pushing the inner catheter forward and forming the desired electrode preshape; deflecting the distal section of the inner catheter about a transverse axis to position the multiple-needle electrode near a target region on an interior wall of the heart chamber; intimately contacting the electrode, including the needles, with the intracardiac tissue; and applying radiofrequency energy to the target location through the needles of this invention.

Another object of the invention is to provide a catheter and methods in which it is possible to view the area to be ablated prior to ablation to ensure that ablation is being carried out in an appropriate location. The electrode having a plurality of needles is encoded with plurality of markers which are visible to ultrasonic energy. The markers have been provided in the form of encapsulated air bubbles. In another embodiment, probes with ultrasonic signal capability are located adjacent to the needle of the said electrode. The ultrasonic signals are directed outwardly and received inwardly relative to the front side of the electrode to permit rapid and substantially continuous viewing of the target tissue.

The method and catheter of the present invention have several significant advantages over known catheter or ablation techniques. In particular, the cooled multiple-needle electrode of a steerable ablation catheter of this invention may result in a plurality of deeper, larger and contiguous lesions which is highly desirable in the AFib treatment.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Figure 1:
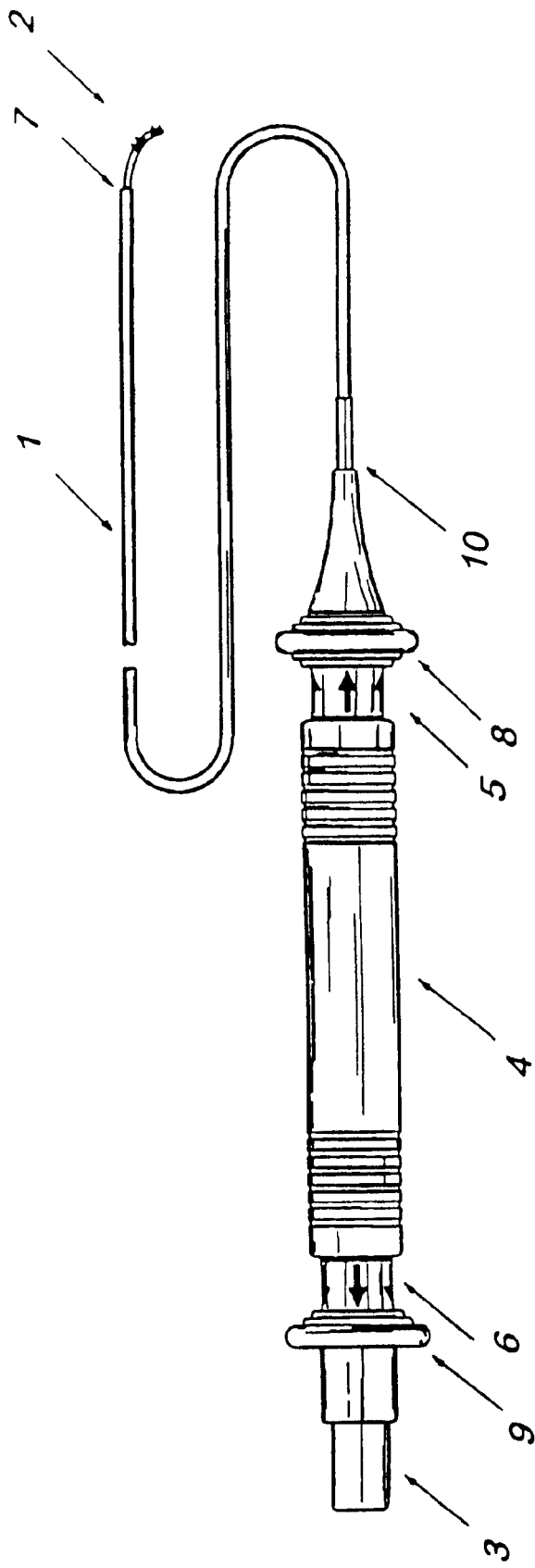
FIG. 1 is an overall view of a catheter having at least one cooled multiple-needle electrode constructed in accordance with the principles of the present invention.

FIG. 1 shows a perspective view of the catheter having a delivery catheter. An ablation catheter constructed in accordance with the principles of the present invention comprises: a delivery catheter 1 having a distal end 7, a proximal end 10, and at least one lumen extending therebetween. The delivery catheter 1 comprises an electrode deployment means, wherein the deployment means comprises a retractable inner catheter 2 having a tip section, comprising at least one cooled multiple-needle electrode. A handle 4 is attached to the proximal end 10 of the said delivery catheter 1.

The connector 3 secured at the proximal end of the catheter system is part of the handle section 4. The handle has one steering mechanism 5 and one inner catheter deployment mechanism 6. The steering mechanism 5 is to deflect the tip section of the inner catheter 2 when the tip section is deployed outside of the distal end 7 of the said delivery catheter 1. By pushing the front plunger 8 of the handle 4, the tip section of the inner catheter deflects to one direction. By pulling the front plunger 8, the tip section returns to its neutral position. In another embodiment, the steering mechanism 5 at the handle 4 comprises means for providing a plurality of deflectable curves on the distal tip section of the inner catheter 2.

The deployment mechanism 6 comprises a catheter shaft for the inner catheter 2, wherein the catheter shaft resists buckling inside the delivery catheter 1. The rear plunger 9 is used to push the tip section of the inner catheter 2 outwards of the delivery catheter 1 during catheter deployment for ablation purpose. While the catheter is introduced into the body or removed from the body of a patient, the tip section of the inner catheter 2 is retracted into the delivery catheter 1 by pulling back the rear plunger 9.

Figure 2:
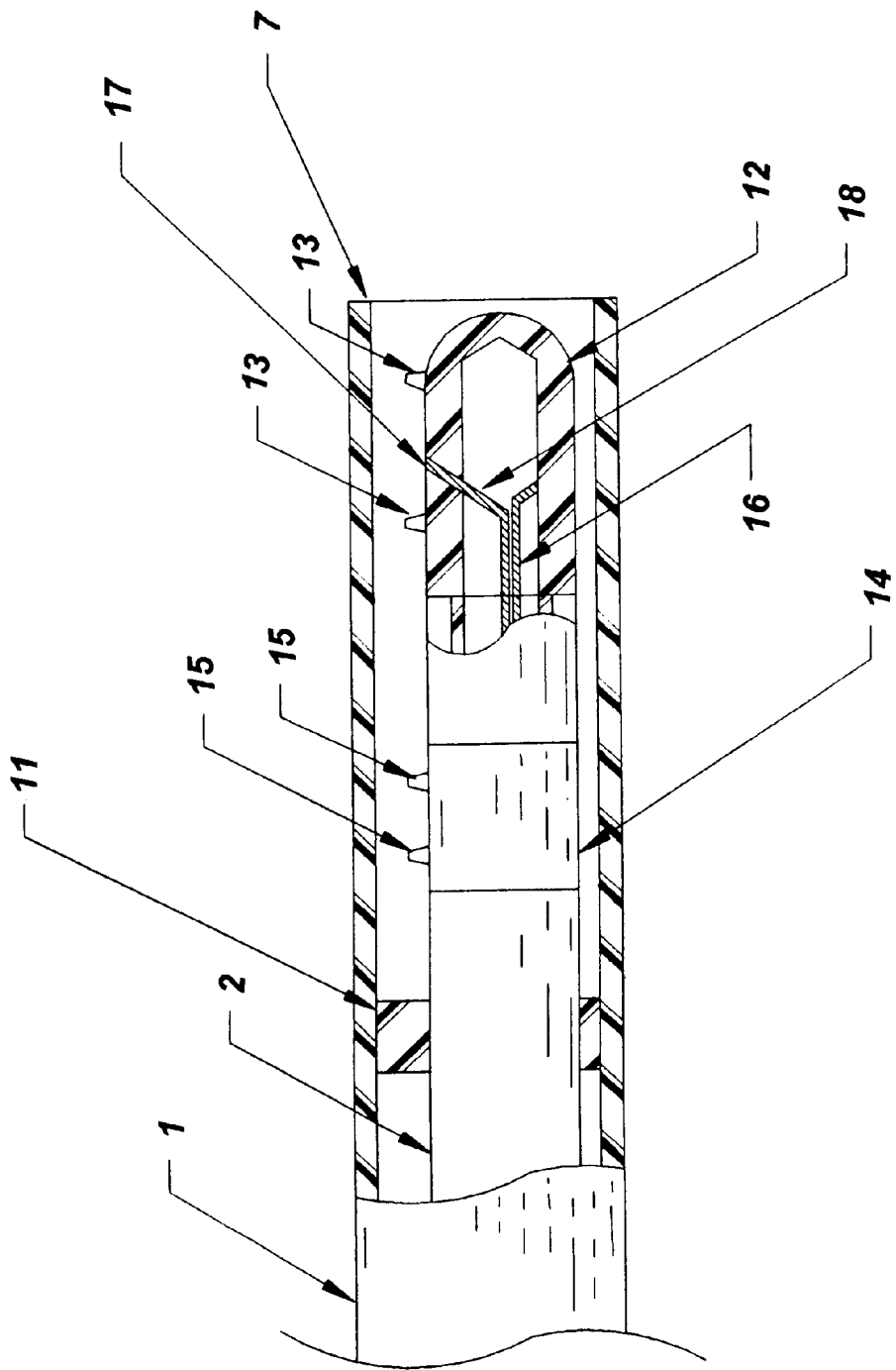
FIG. 2 is a closeup view of the distal section of the catheter at nondeployed state.

FIG. 2 shows a closeup view of the distal section of the catheter at nondeployed state of FIG. 1. The tip section of the delivery catheter comprises a distal end 7 and a sealable opening 11. The tip section of the inner catheter 2 comprises a tip electrode 12 which has a plurality of flat top needles 13, and at least one band electrode 14 which has a plurality of flat top needles 15. The electrodes are formed of a conducting material. In one embodiment, at least one electrode is a metal mesh or a metal coil securely wrapped outside of the catheter shaft of the inner catheter 2, wherein the electrode has a plurality of needles 14 or 15. To prevent blood from backflow into the delivery catheter 1, a silicone type sealer 11 is installed at certain opening of the delivery catheter between the delivery catheter 1 and the inner catheter 2.

Figure 3:
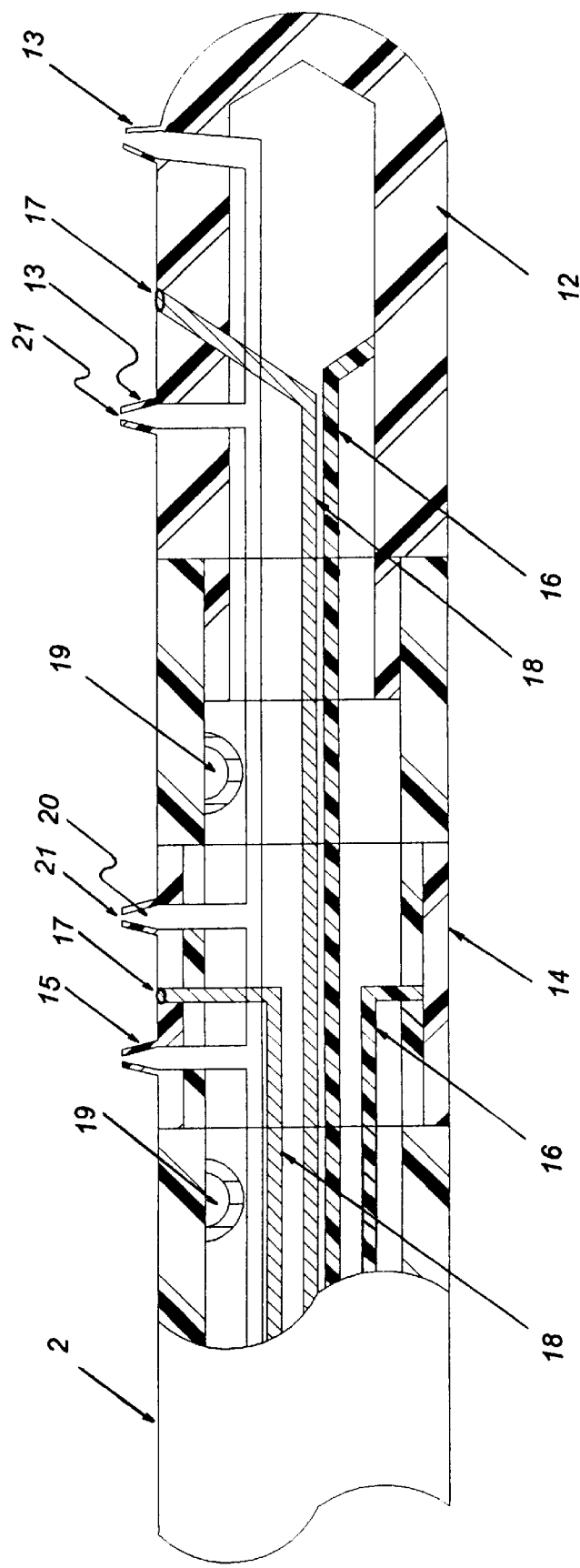
FIG. 3 is a cross-sectional view of the tip section of the inner catheter having cooled multiple-needle electrodes.

FIG. 3 shows a cross-sectional view of the tip section with at least one temperature sensor 17 and ultrasonic imaging capabilities. In order to enhance the ablation positioning of the said ablation catheter, the electrode is encoded with markers 19 which are visible to ultrasonic energy. Such markers 19 are provided in the form of encapsulated air bubbles. Several markers 19 are placed on the same side of the needles relative to the inner catheter shaft and in the proximity of the needles 15 of the multiple-needle electrode 14 in a way so that the exact location of the needles 15 is visible to an external ultrasonic energy. By way of example, the bubble in a marker can be formed by introducing air by a syringe (not shown) penetrating the wall of the plastic shaft of the said inner catheter and thereafter is sealed by epoxy.

The multiple-needle electrode has an insulated conducting wire 16 secured to the electrode which passes through the lumen of the inner catheter 2 and is soldered to a contact pin of the connector 3 at the proximal end of the handle 4. The conducting wire from the connector end is externally connected to an EKG for diagnosis or to an RF generator during an electrophysiology ablation procedure. Therefrom, the RF energy is transmitted through the conducting wire to the multiple-needle electrode and delivered the energy to the target tissue.

A temperature sensor 17, either a thermocouple means or a thermister means, is constructed at the proximity of one needle 13 or 15 of the electrodes 12 or 14 to measure the tissue contact temperature when RF energy is delivered. The temperature sensing wire 18 from the thermocouple or thermister is connected to one of the contact pins (not shown) of the connector 3 and externally connected to a transducer and to a temperature controller. The temperature reading is thereafter relayed to a close-loop control mechanism to adjust the RF energy output. The RF energy delivered is thus controlled by the temperature sensor reading or by a preprogrammed control mechanism.

The tip section having at least one multiple-needle electrode formed of conducting material can be extended out of the delivery catheter 1 and retracted into the said delivery catheter by a deployment mechanism 6 at the handle 4.

A plurality of needles 14 or 15 on the at least one electrode have a needle structure comprising a hollow passage 20 with an outlet port 21; and means formed within the needle structure for providing fluid communication and commensurate flow of fluid originating inside the needle structure to portions of the electrode exterior surface through a plurality of passages 20 and outlet ports 21 which direct the fluid flow from inside the inner catheter shaft over the exterior surface of the needles to provide a fluid protective layer surrounding the electrode to minimize temperature elevation of the electrode with biological tissues.

Figure 4:
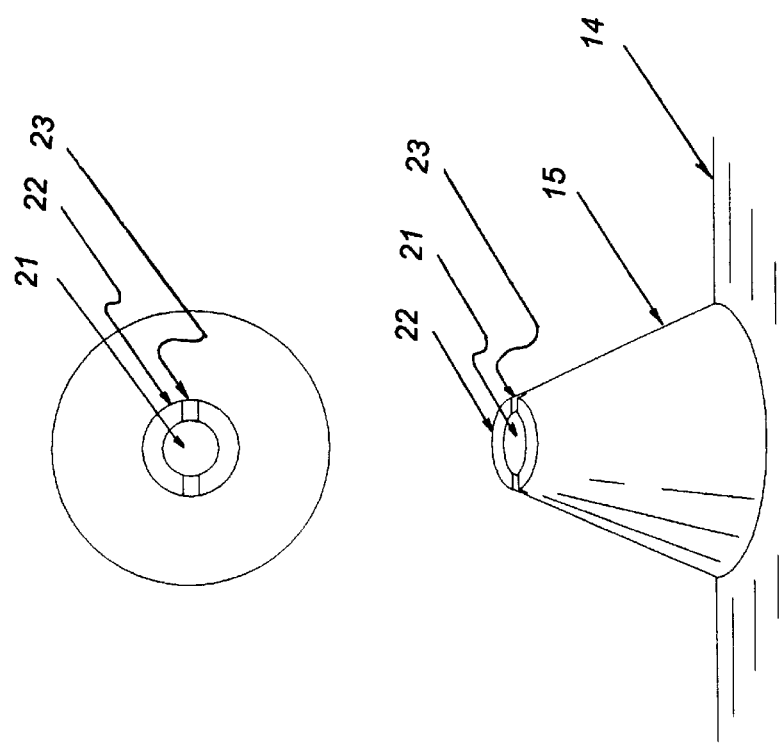
FIG. 4 is a perspective view of the flat top needle of the electrodes of the inner catheter of FIG. 1.
Figure 5:
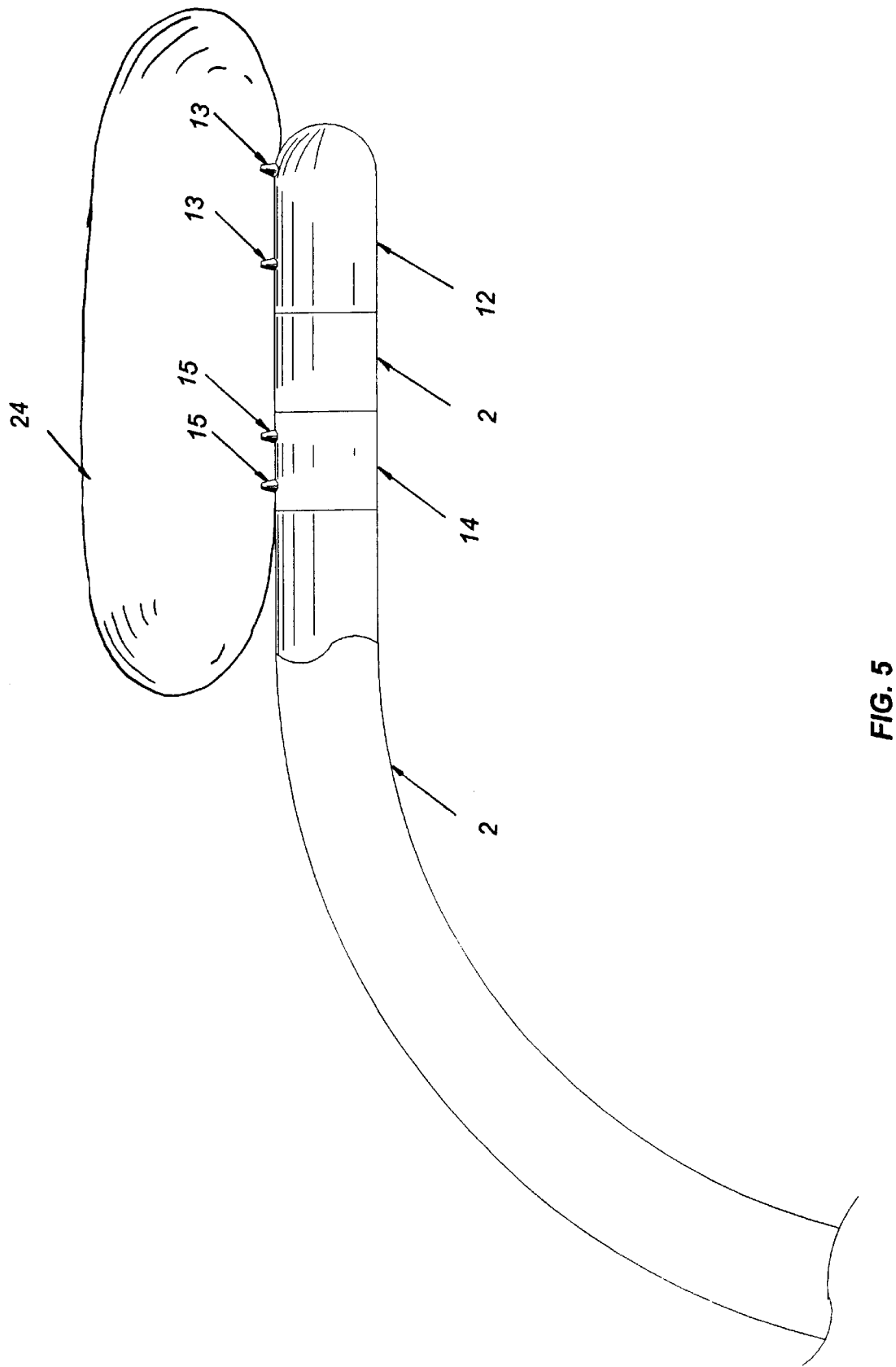
FIG. 5 shows the contact of the cooled multiple-needle electrodes of the catheter of this invention with the tissue.

FIG. 4 shows a perspective view of the needles of the multiple-needle electrode of the inner catheter, wherein the needle comprises a flat top 22, and at least one drainage trough 23 at its flat top. FIG. 5 shows the contact of the needles 13 and 15 of the cooled multiple-needle electrodes 12 and 14 with the target tissue 24. The needle may contact the tissue at an angle essentially perpendicular to the target tissue. RF energy is applied thereafter while a cooled fluid is provided either simultaneously or intermittently. A plurality of deep and large lesions are created which are contiguous for the treatment of a tachycardia.

From the foregoing, it should now be appreciated that a method employing an improved ablation catheter having multiple-needle electrode and a cooling fluid capability has been disclosed for ablation procedures, including endocardial, epicardial, or body tissue ablations. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A method for operating a steerable ablation catheter having at least one multiple-needle electrode at the tip section of an inner catheter within a heart chamber, the ablation catheter comprising a delivery catheter having a distal end, a proximal end, and at least one lumen extending therebetween; a handle attached to the proximal end of the delivery catheter; an inner catheter located within the lumen of the delivery catheter, having a distal tip section, a distal end, a proximal end, and a central lumen extending therebetween, wherein the distal tip section has at least one electrode; a plurality of needles on the at least one electrode which form a multiple-needle electrode, wherein each needle has a needle structure comprising a hollow passage with an outlet port; RF energy generating means connected to the at least one needle electrode, wherein the RF energy is delivered to the needles of the multiple-needle electrode; and means formed within the needle structure for providing fluid communication and commensurate flow of fluid originating inside the needle structure to portions of the exterior surface of the said at least one electrode through the said hollow passage which direct the fluid flow from inside the central lumen of the inner catheter over the exterior surface of the needles to provide a fluid protective layer surrounding the electrode to minimize temperature elevation of the electrode with biological tissues;

the method comprising the steps of:
 (a) percutaneously introducing the delivery catheter through a blood vessel to the heart chamber, wherein the multiple-needle electrode is deployed by pushing the inner catheter forward;
 (b) deflecting the distal section of the inner catheter about a transverse axis to position the multiple-needle electrode near a target on an interior wall of the heart chamber;
 (c) intimately contacting the electrode with the intracardiac tissue;
 (d) applying RF energy for ablation; and
 (e) cooling the electrodes by releasing cooled fluid through the openings of the needles.

2. The method for operating an ablation catheter of claim 1, wherein at least one multiple-needle electrode is formed of a metal mesh.

3. The method for operating an ablation catheter as in claim 1 further comprising a close-loop temperature control mechanism for the multiple-needle electrode having at least one temperature sensor mounted on the multiple-needle electrode and providing sensing signals for the close-loop controller.

4. The method for operating an ablation catheter of claim 1, wherein a longitudinal length of the said at least one multiple-needle electrode is at least 4 mm.

5. The method for operating an ablation catheter as in claim 1 further comprising a plurality of ultrasonic visible markers being disposed at close proximity to the needles of the multiple-needle electrode.

* * * * *